(12) United States Patent
Axelgaard

(10) Patent No.: US 10,980,994 B2
(45) Date of Patent: Apr. 20, 2021

(54) DUAL-SIDED ELECTRODE PAD

(71) Applicant: Jens Axelgaard, Fallbrook, CA (US)

(72) Inventor: Jens Axelgaard, Fallbrook, CA (US)

( * ) Notice: Subject to any disclaimer, the term of this patent is extended or adjusted under 35 U.S.C. 154(b) by 21 days.

(21) Appl. No.: 15/415,621

(22) Filed: Jan. 25, 2017

(65) Prior Publication Data

US 2017/0209684 A1 Jul. 27, 2017

Related U.S. Application Data

(60) Provisional application No. 62/287,393, filed on Jan. 26, 2016.

(51) Int. Cl.
*A61N 1/04* (2006.01)

(52) U.S. Cl.
CPC ......... *A61N 1/0492* (2013.01); *A61N 1/0452* (2013.01)

(58) Field of Classification Search
CPC .............................. A61N 1/0492; A61N 1/0452
See application file for complete search history.

(56) References Cited

U.S. PATENT DOCUMENTS

| | | | |
|---|---|---|---|
| 4,870,969 A * | 10/1989 | Swartz | A61N 1/0408 607/45 |
| 5,904,712 A | 5/1999 | Axelgaard | |
| 6,038,464 A | 3/2000 | Axelgaard et al. | |
| 6,038,485 A | 3/2000 | Axelgaard | |
| 6,438,428 B1 | 8/2002 | Axelgaard et al. | |
| 6,571,115 B2 | 5/2003 | Axelgaard et al. | |
| 7,346,380 B2 | 3/2008 | Axelgaard et al. | |
| 7,729,779 B2 * | 6/2010 | Babaev | A61N 1/0456 607/115 |
| 7,769,473 B2 | 8/2010 | Axelgaard | |
| 8,473,072 B2 | 6/2013 | Axelgaard | |
| 8,874,231 B2 | 10/2014 | Axelgaard | |
| 2001/0051821 A1 * | 12/2001 | Snyder | A61B 5/04087 607/142 |
| 2002/0156357 A1 * | 10/2002 | Axelgaard | A61B 5/0416 600/391 |
| 2003/0055478 A1 * | 3/2003 | Lyster | A61N 1/046 607/142 |

(Continued)

*Primary Examiner* — Catherine M Voorhees
*Assistant Examiner* — Roland Dinga
(74) *Attorney, Agent, or Firm* — Hackler Daghighian Martino & Novak

(57) ABSTRACT

A dual-sided electrode pad assembly is configured to be placed upon a patient's skin and includes an upper conductive gel layer, a middle conductive layer comprising a highly conductive foil, a highly conductive plastic film or a gel with suspended highly conductive particles, and a lower conductive gel layer. The upper and lower conductive gel layer comprise hydrogel, silicone or hydrocolloid. A removable upper and lower protective liner are disposed on the upper and lower conductive gel layers, wherein the upper and lower protective liners are larger in surface area in comparison to the upper conductive gel layer, the middle highly conductive layer and the lower conductive gel layer. The middle highly conductive layer may be smaller in surface area in comparison to the upper and lower conductive gel layers allowing a perimeter edge of the upper and lower conductive gel layers to be disposed past a perimeter edge of the middle highly conductive layer.

36 Claims, 6 Drawing Sheets

(56) References Cited

U.S. PATENT DOCUMENTS

| | | | |
|---|---|---|---|
| 2004/0249432 A1* | 12/2004 | Cohen .................. | A61N 1/0452 |
| | | | 607/149 |
| 2005/0015134 A1* | 1/2005 | Carim .................. | A61B 5/0408 |
| | | | 607/142 |
| 2007/0238944 A1* | 10/2007 | Axelgaard ........... | A61N 1/0452 |
| | | | 600/372 |
| 2009/0209840 A1 | 8/2009 | Axelgaard | |
| 2009/0278815 A1* | 11/2009 | Li ......................... | G06F 3/045 |
| | | | 345/174 |

* cited by examiner

DUAL-SIDED ELECTRODE PAD

CROSS-REFERENCE TO RELATED APPLICATIONS

This non-provisional application claims priority to provisional application 62/287,393 filed Jan. 26, 2016, the entire contents of which are hereby incorporated by reference.

FIELD OF THE INVENTION

The present invention generally relates to electrodes. More particularly, the present invention relates to a dual-sided electrode pad.

BACKGROUND OF THE INVENTION

In the prior art an ELECTRICAL STIMULATION ELECTRODE was taught in U.S. Pat. No. 6,438,428 issued on Aug. 20, 2002, the contents of which are fully incorporated in full herein with this reference. Referring now to FIG. 4, it showed an exploded view of an electrical pad 40. Each conductive pad 40 included a cover electrically conductive gel adhesive layer 42, a current controlling media 50 and a base electrically conductive gel adhesive layer 56. As you can see in FIG. 4, all of these layers ended at the same perimeter location. These electrodes 40 are typically used with a garment or brace that helps hold the electrodes 40 into place, as is taught in the '428 patent. When the electrodes 40 are not in use, they may be stored for later use. A problem with this design is that the edge of layer 50 may come into contact with skin of the user/patient during use. This may then lead to localized heating or undesirable hot spots.

Then, in the prior art a COMPRESS GARMENT FACILITATING THE USE OF MEDICAL ELECTRODES was taught in U.S. Pat. No. 6,571,115 issued on May 27, 2003, the contents of which are fully incorporated herein with this reference. Referring now to FIG. 14, it showed how the current controlling media no longer came to an edge, but rather had a border section disposed around the perimeter. This then eliminated localized heating and undesirable hot spots because there was a perimeter border area of low conductivity for the current controlling media layer. However, this resulted in an expensive electrode construction due to the added printing of a conductive pattern.

Accordingly, there is a need for an improved electrode that overcomes the drawbacks of the prior art. The present invention fulfills these needs and provides other related advantages.

SUMMARY OF THE INVENTION

An exemplary embodiment of the present invention is a dual-sided electrode pad assembly configured to be placed upon a patient's skin, the dual-sided electrode pad assembly comprising: an upper conductive gel layer; a middle conductive layer comprising a metallic foil layer, a graphite layer or any highly conductive current distribution media; and a lower conductive gel layer; wherein the middle conductive layer is disposed between the upper and lower conductive gel layers.

In other exemplary embodiments, the upper conductive gel layer may be 5 to 50 mils thick, or the upper conductive gel layer may typically be approximately 20 mils thick. The upper conductive gel layer may comprise hydrogel, silicone or hydrocolloid.

In other exemplary embodiments, the middle conductive layer may be 0.1 to 10 mils thick, or the middle conductive layer may typically be approximately 1 mil thick. The middle highly conductive foil layer may comprise aluminum, tin, graphite, graphene or any highly conductive material.

In other exemplary embodiments, the lower conductive gel layer may be 20 to 120 mils thick, or the lower conductive gel layer may typically be 40 mils thick. The lower conductive gel layer may comprise hydrogel, silicone or hydrocolloid.

In other exemplary embodiments, a removable upper protective liner may be disposed on the upper conductive gel layer, wherein the upper protective liner is larger in surface area in comparison to the upper conductive gel layer, the middle conductive layer and the lower conductive gel layer. Furthermore, a removable lower protective liner may be disposed on the lower conductive gel layer, wherein the lower protective liner is larger in surface area in comparison to the upper conductive gel layer, the middle conductive layer and the lower conductive gel layer.

In other exemplary embodiments, the upper conductive gel layer may be smaller in surface area in comparison to the middle conductive layer allowing a perimeter edge of the middle conductive layer to be disposed past an edge of the upper conductive gel layer. The lower conductive gel layer may be larger in surface area in comparison to the middle conductive layer allowing a perimeter edge of the lower conductive gel layer to be disposed past the perimeter edge of the middle conductive layer.

In other exemplary embodiments, the upper conductive gel layer and the middle conductive layer generally may have the same size of surface area, and wherein the lower conductive gel layer is larger in surface area in comparison to the upper conductive gel layer and the middle conductive layer allowing a perimeter edge of the lower conductive gel layer to be disposed past an edge of the upper conductive gel layer and the middle conductive layer.

In other exemplary embodiments, the middle conductive layer may be smaller in surface area in comparison to the upper and lower conductive gel layers allowing a perimeter edge of the upper and lower conductive gel layers to be disposed past a perimeter edge of the middle conductive layer.

In other exemplary embodiments, the middle conductive layer may comprise an indicia. The indicia may be embossed into the middle conductive layer. The indicia may be laser etched onto the middle conductive layer. The indicia may be printed onto the middle conductive layer.

In other exemplary embodiments, the middle conductive layer may comprise a plurality of individual middle conductive layers disposed between the upper and lower conductive gel layers.

In other exemplary embodiments, at least one cutout may be formed in the middle conductive layer. The at least one cutout may be formed in either the upper or lower conductive gel layers. The at least one cutout may similarly be formed in the upper conductive gel layer, the middle conductive layer and the lower conductive gel layer. The cutout may comprise the shape of a circle, square, rectangle, triangle, oval, ellipse, quatrefoil, curvilinear triangle, trapezoid, rhombus, kite, pentagon, hexagon, heptagon, octagon, nonagon, decagon, parallelogram or crescent.

In other exemplary embodiments, the electrode may include at least one ink pattern disposed on the middle conductive layer, wherein the at least one ink pattern comprises a higher resistivity in comparison to the middle conductive layer. In another embodiment the conductive foil or the conductive plastic film may comprise at least two materials with differing resistivities. Alternatively, the suspended conductive particles of the gel layer may comprise at least two materials with differing resistivities. As can be seen, these are all embodiments of structures which can be used to control current distribution in the present invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
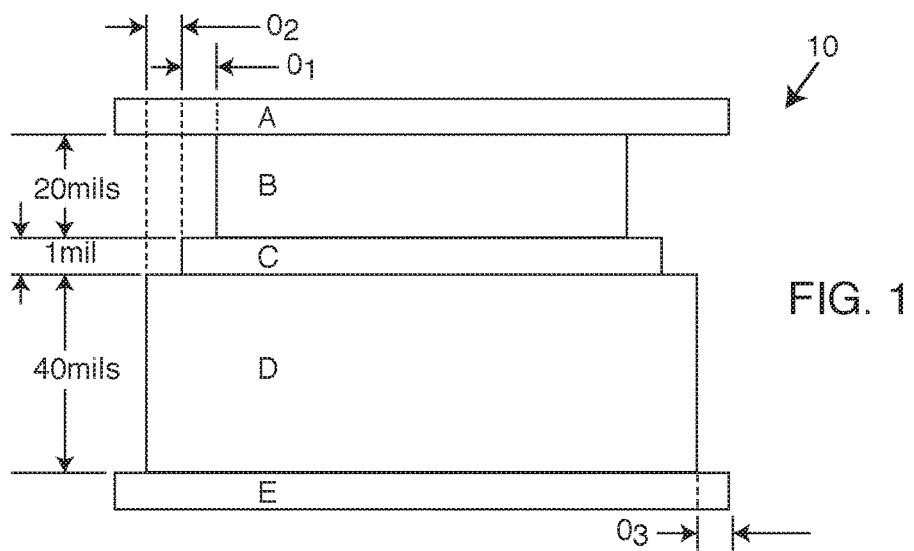
FIG. 1 is a sectional view through an exemplary electrode of the present invention.

FIG. 1 is a cross-sectional view of a new embodiment of a dual-sided electrode pad assembly 10 of the present invention. FIG. 1 is not drawn to scale, but rather is drawn substantially thicker for simplicity to convey the concepts and teachings of the present invention.

Layer A is a protective liner that is removed before the electrode itself is utilized. Layer A is significantly oversized in its surface area (i.e. its diameter or width of the electrode) such that it extends beyond the other active layers B, C, and D. This allows easy removal of layer A when the electrode itself is to be used. Layer A is typically a translucent blue silicone liner of medium-density polyethylene at 2-3 mils thick.

Layer E is also a protective liner that is removed before the electrode itself is used. Layer E may be made from polyester (Mylar) or other suitable liner materials known to those skilled in the art. Layer E is also oversized, normally 2-5 mils thick, making it easy to place the silicone coated film on the skin-side gel when the electrode 10 is not in use. The Mylar is usually colored or printed with instructions in a manner making it visible should it fall on the floor thus preventing falls in the slippery silicone.

Layers A and E protect the electrode 10 during shipping and storage. Layers A and E also prevent dust, particles and other contaminates from dirtying the electrode 10. Also, layers A and E prevent the adhesive gels B and D from sticking to other objects. Layers A and E help prevent the electrode 10 from drying out as layers B and D are typically conductive hydrogel layers which could dry out if left uncovered. Therefore, even after the electrode 10 itself is used, layers A and E can be reused to further protect the electrode 10 until the electrodes next usage.

Layers B and D are conductive gels. In this embodiment layer B is about 20 mils thick, but can be made within a range of 5-50 mils thick. Layer D is about 40 mils thick, but can be made in a range of 20-120 mils thick. The conductive gels for layers B and D may be made from any conductive adhesive such as hydrogel, silicone, hydrocolloid, etc. as an example. See prior art MEDICAL ELECTRODE as taught in U.S. Pat. No. 7,346,380 issued on Mar. 18, 2008, which is incorporated in full herein with this reference.

In the prior art U.S. Pat. No. 6,571,115, the current controlling media 50 was a printed carbon film which was expensive to produce. In the present invention, layer C is a conductive metallic foil, a graphite layer or any other highly conductive media. The thickness of layer C can be around 1 mils, or in a range of 0.1-10 mils. The use of a 1 mil aluminum foil in layer C significantly reduces the cost of the overall electrode assembly 10.

As can be seen in FIG. 1, layer B is smaller in surface area (i.e. its diameter or width/length across the electrode) in comparison to layer C, which can be seen in the oversize one dimension ($O_1$). Then layer C is smaller in surface area in comparison to layer D, which can be seen in the oversize two dimension ($O_2$). Also, layers A and E are oversized in comparison to layers B, C and D, which can be seen in the oversize three dimension ($O_3$). In this embodiment, the differing surface areas of the active layers prevents and/or reduces the chance of edge burning or undesirable localized heating. The B layer may be of any size smaller than the C layer ($O_1$) while the D layer preferably is ¼" larger along the edge than the C layer but may be in an oversize range of ⅛" to ⅝" ($O_2$). The A and E layers in one embodiment may be ¼" or longer ($O_3$) than the D layer, but may be a minimum oversize equal to or greater than ⅛".

As shown in FIG. 1, layer B is smaller in surface area in comparison to layers C and D. However, in other embodiments layer B may be the same size as layer C, where then layer D is oversized ($O_4$) in comparison to layers B and C. This embodiment is best shown in FIG. 2.

Figure 3:
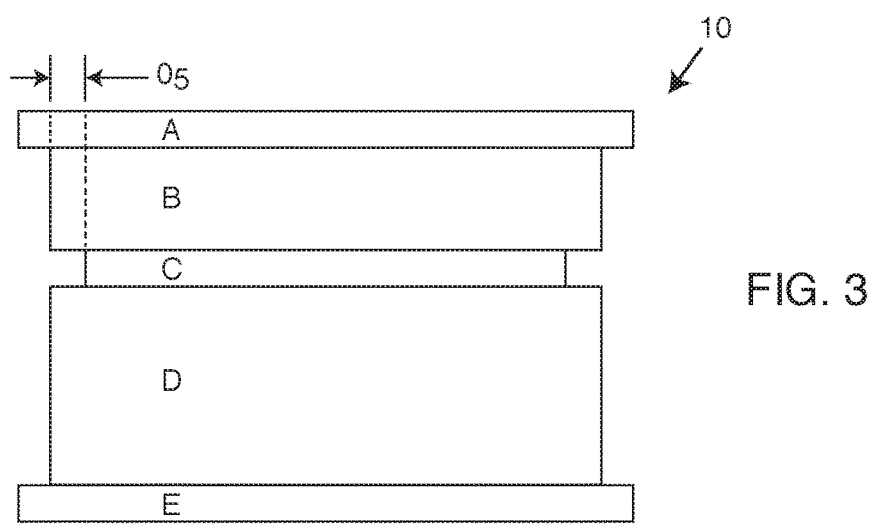
FIG. 3 is a sectional view through yet another exemplary electrode of the present invention.

Alternatively, layer B may be the same size (surface area) as layer D, where now layers B and D are oversized ($O_5$) in comparison to layer C. This embodiment is best shown in FIG. 3. In all of these embodiments, the chance of edge burning or undesirable localized heating is either reduced and/or eliminated.

FIG. 3 also teaches a significant advantage in safety for use of the electrode 10. It some situations, the electrode may be placed upside-down by the user/patient. This may occur through unintentional error during use, as one may be fatigued or not paying close attention. FIG. 3 shows that both layers B and D are oversized in comparison to layer C. This unique structure then allows the electrode in FIG. 3 to be placed upside-down and still not create hot spots or undesirable localized heating.

Figure 2:
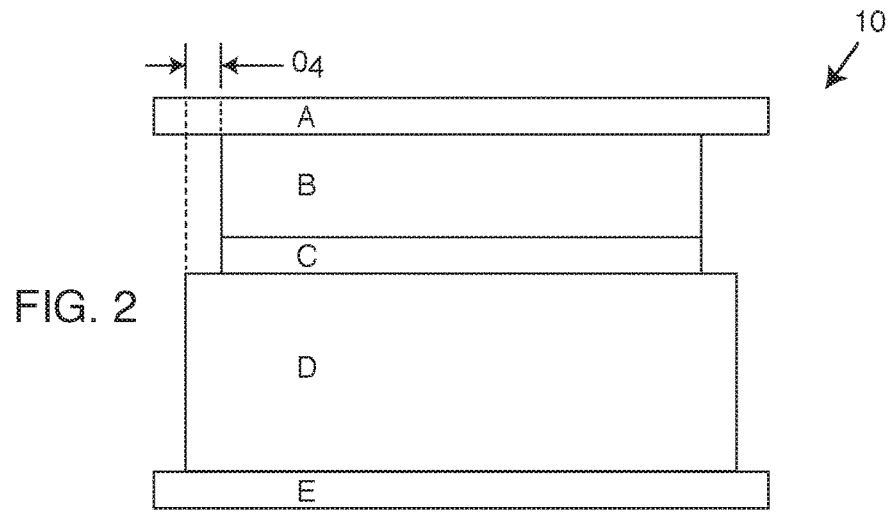
FIG. 2 is a sectional view through another exemplary electrode of the present invention.

As can be understood and seen in FIG. 1-3, it is no longer needed that a printed carbon film with an unprinted border be used. Rather now, a conductive foil can be used instead, such a metallic foil, a graphite foil or any other highly conductive cheaper media can be used. For example a conductive plastic film layer can be used herein with the present invention. Furthermore, a hydrogel layer may be used wherein the hydrogel layer comprises a suspended metal, graphite, graphene or other highly conductive particles. The conductive particles can not only be suspended in hydrogel but also in a silicone or hydrocolloid gel layer.

Figure 4:
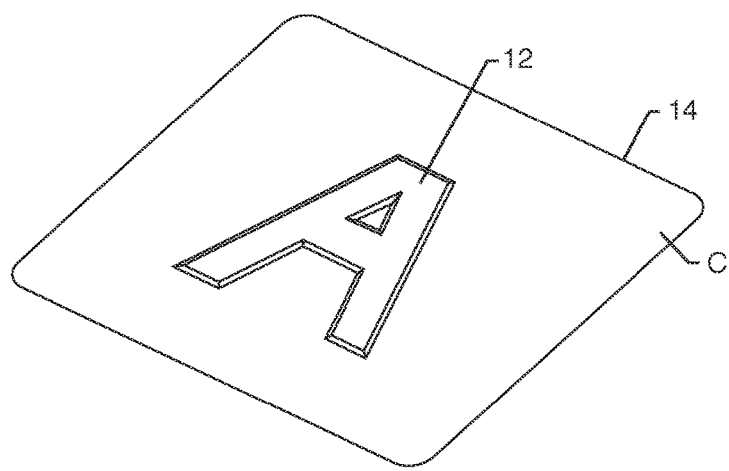
FIG. 4 is a perspective view of layer C with an embossed indicia.

Referring now to FIG. 4, in another embodiment it is possible to emboss layer C with various indicia 12 that may be useful to the user or the manufacturer. For example, layer C may be embossed with a logo or trademark 12 to help identify the manufacturer of the electrode. Or, layer C may be embossed with various directions that help the user utilize the electrode 10. In another embodiment, embossing layer C may be done when layer C has a thickness of around 1 mil, but it is also possible to emboss other thicknesses. It is possible to see such embossed structures because it is typical that layers B and/or D are at least partially optically transparent such that a user can see what is embossed on layer C.

It is also possible that during the step for embossing, that the layer C can be cutout 14 at the same time. For example, in manufacturing the embossing step 12 and cutout step 14 can be one after the other, or done at the same time to speed up the manufacturing process.

Figure 5:
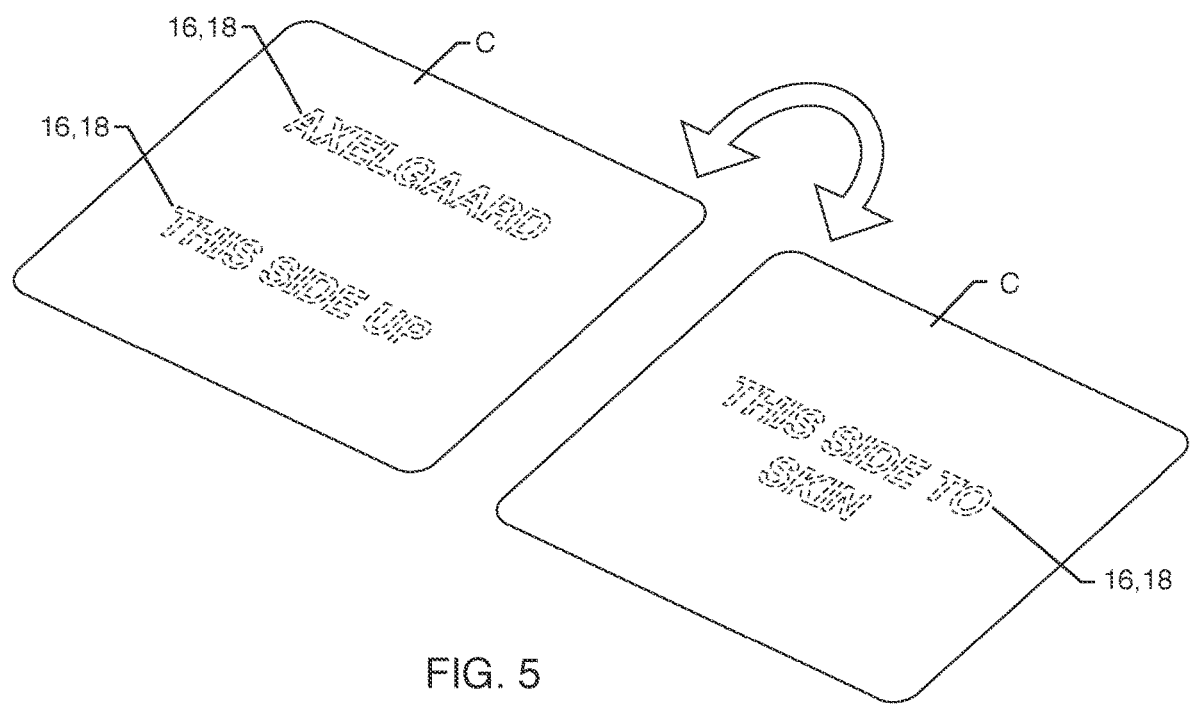
FIG. 5 is an perspective view of both sides of layer C with either laser etched or printed indicia.

Referring now to FIG. 5, in another embodiment it is possible to laser etch various indicia 16 into the layer C. Laser etching can produce very accurate and detailed information 16. Again, various logos or directions can be laser etched directly onto layer C.

In another embodiment, it is possible to print various indicia 18 onto layer C. Printing can also produce very accurate and detailed information.

As an example of the present invention, when layer C is changed from a carbon film at $0.70/LnFt (linear foot) to now $0.02/LnFt for an aluminum foil, a substantial reduction in cost is achieved (a factor 35). This change in material combined with a new oversized configuration taught in FIGS. 1-3 is a significant improvement over the prior art.

Figure 6:
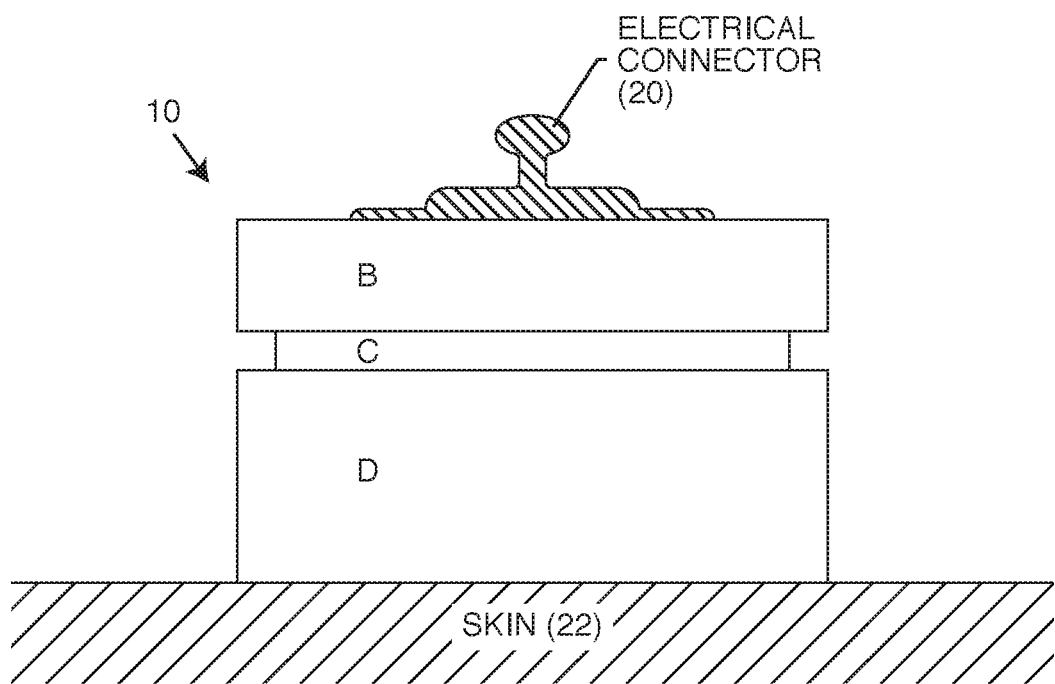
FIG. 6 is a sectional view of the exemplary electrode of FIG. 3 now placed upon a patient.
Figure 7:
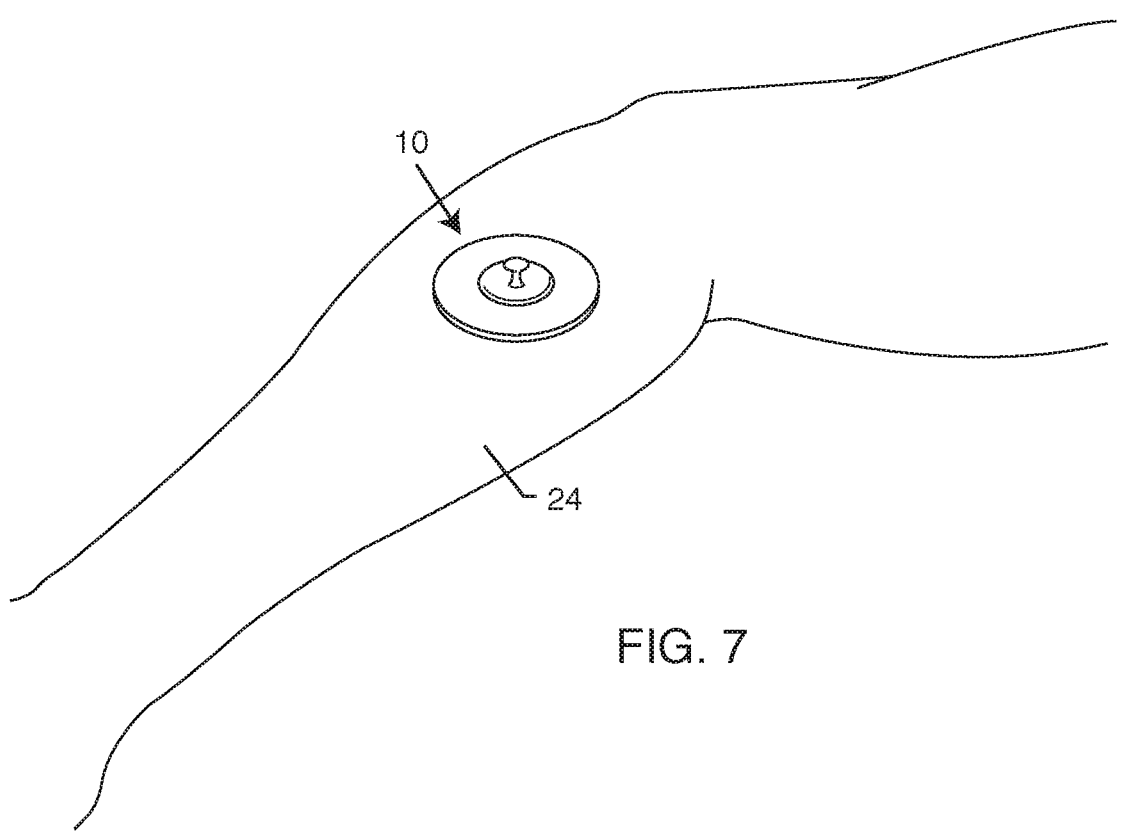
FIG. 7 is an perspective view of an exemplary electrode of the present invention placed upon a patient's forearm.

Referring now to FIGS. 6 and 7 it is also important to understand that the embodiments of the present invention can be used with a garment or brace as in the prior art, but can also be utilized without such garment or braces. For example, the electrode 10 of the present invention can be utilized with any electrical connection means 20 that conducts electrical signals to layer B, which then conducts through layers C and D and finally to the skin 22 of the user/patient. Therefore, the use of a garment or brace is not required to practice the embodiments of the present invention taught herein.

FIG. 7 shows the electrode 10 in a more realistic perspective view placed upon a forearm 24 of the user/patient.

Figure 8:
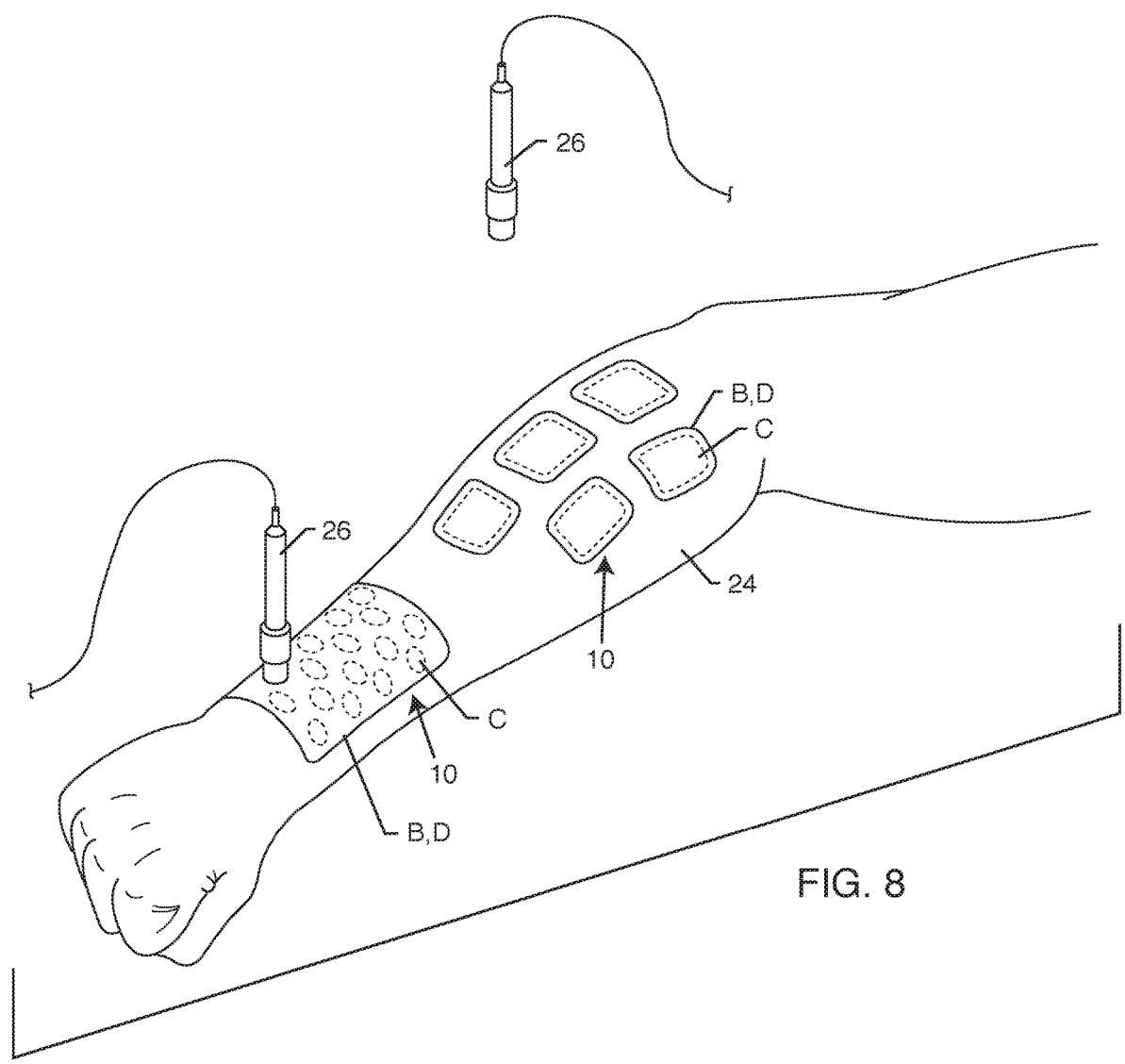
FIG. 8 is similar to FIG. 7, now showing multiple electrodes placed upon a patient's forearm with probes to selectively activate certain electrodes.

Referring now to FIG. 8, a plurality of dual-sided electrodes 10 may be placed on the skin by a physical therapist, as seen in the upper forearm location where the B and D layers are oversized in comparison to the C layer. As also shown in FIG. 8 near the wrist, a substantially large B and D layer contains a plurality of smaller C layers in between. As can be seen in FIG. 8, with reference to FIGS. 1-3, there are a multitude of ways the present invention can be configured into varying types of electrodes. It is then understood by those skilled in the art that any of the electrode embodiments taught herein (FIGS. 1-3) may be used in the above described methods.

Typically for muscle stimulation, two electrode locations are used to elicit proper muscle contractions for muscles in-between these electrode locations when stimulated. For example one probe 26 may activate an electrode on the upper forearm whereas a second probe 26 may activate an electrode near the wrist. Therefore, the two probes 26 can then be used to activate certain muscles for stimulation. By moving the two probes 26 from electrode pair to electrode pair, the practitioner may quickly and accurately by comparison determine the optimum permanent electrode placements for then the actual treatment electrodes. This is similar in concept to FIG. 6 of U.S. Pat. No. 5,904,712 issued on May 18, 1999 and FIG. 6 of U.S. Pat. No. 6,038,485 issued on Mar. 14, 2000, the contents of which are fully incorporated herein with this references.

Figure 9:
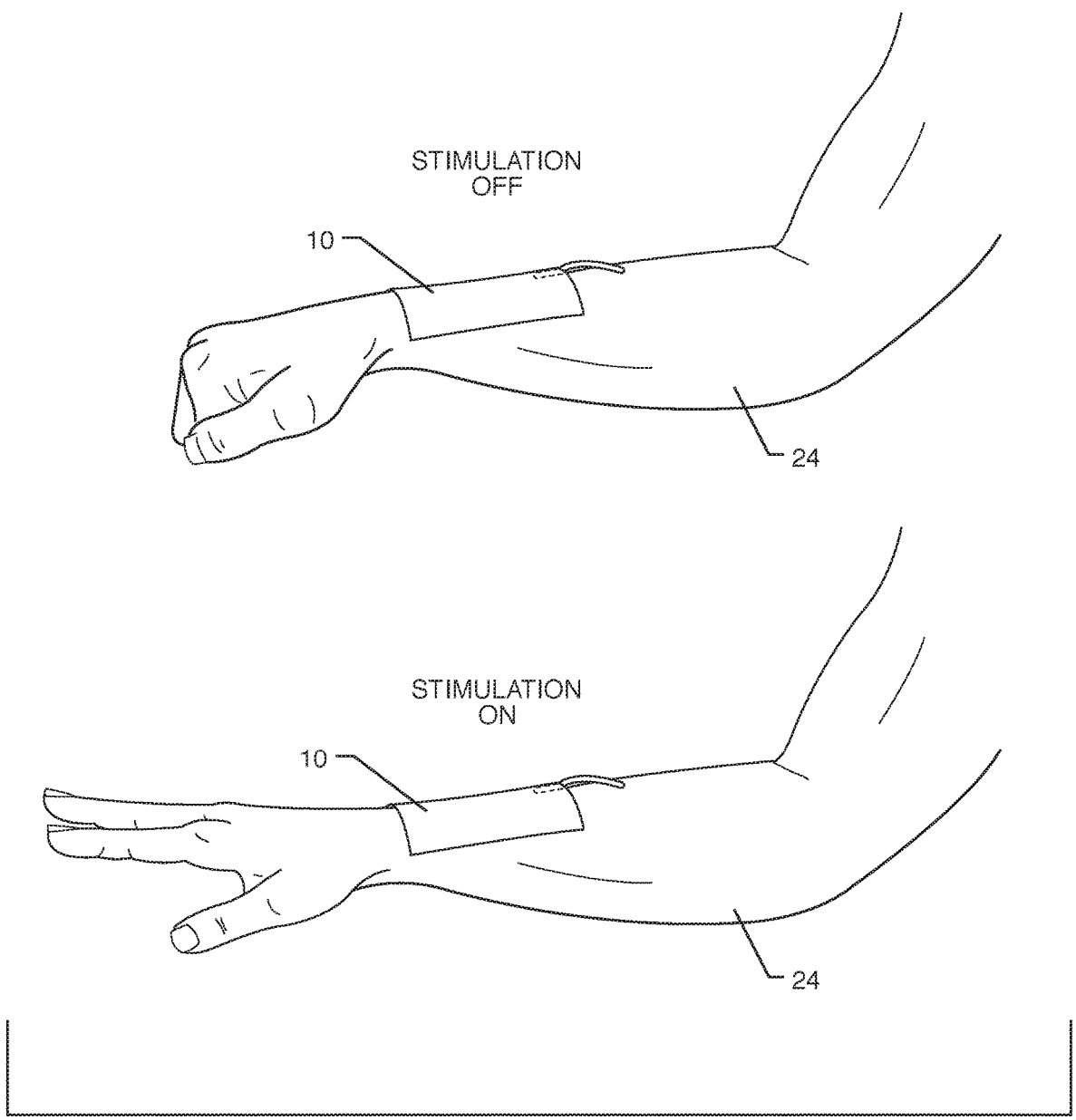
FIG. 9 is a perspective view of the electrodes of the present invention in the stimulating and non-stimulating states.

To better help the reader understand how the electrodes work in practice, one is referred to FIG. 7 of U.S. Pat. No. 8,473,072 issued on Jun. 25, 2013 and U.S. Pat. No. 8,874,231 issued on Oct. 28, 2014, the contents of which are fully incorporated herein with this references. This is also shown herein in the present invention as FIG. 9. FIG. 9 is a perspective view of an electrode 10 attached to the forearm 24 of a patient. In the upper view the electrode is in an off state and is not transmitting any electrical signals. The hand of the patents is shown in a closed state. The lower view shows the electrode in an activated state and accordingly the hand of the patient is open. As can be understood by those skilled in the art, the electrode 10 can be configured to be placed along any other body part of the patient.

Figure 10:
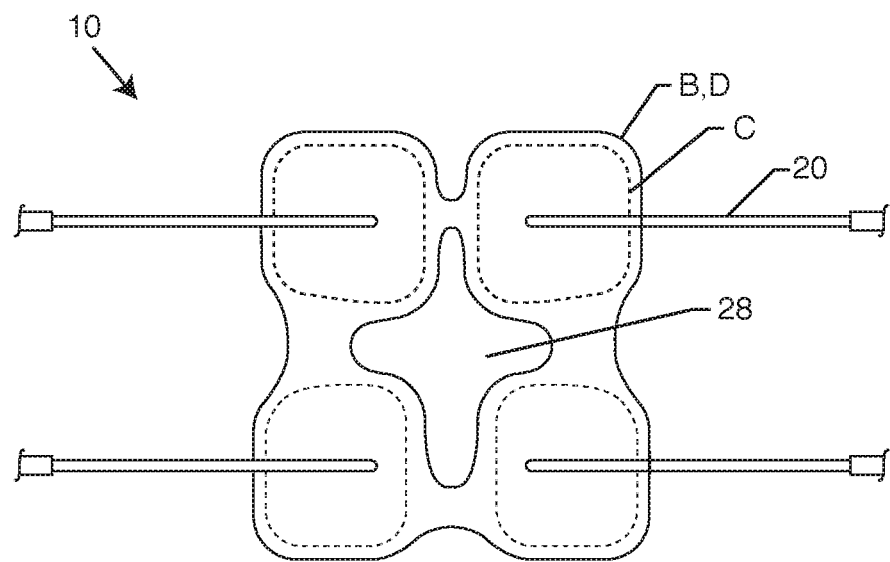
FIG. 10 is a top view of another embodiment of the present invention showing the electrode can include a multitude of sections and also include a cutout.
Figure 11:
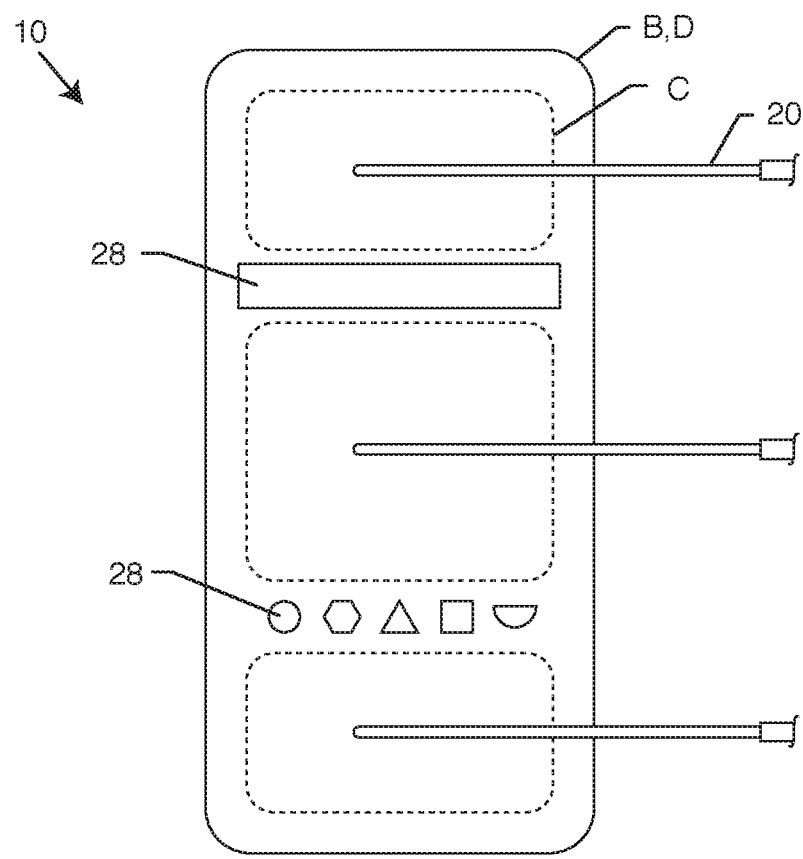
FIG. 11 is a top view of yet another embodiment of the present invention showing the electrode can include a multitude of sections and cutouts of varying sizes and shapes.

The present invention can also be designed to incorporate various cutouts or voids that can be formed in any of the layers B, C or D. For example, FIG. 10 illustrates a view similar to that of FIG. 9 in U.S. Patent Publication 2007/0238944, the contents of which are fully incorporated herein. FIG. 10 is a top view of another embodiment of an electrode 10 of the present invention where a cutout 28 is formed between four separately controlled electrodes. FIG. 11 of the present invention is also similar to FIG. 8 of the '944 patent publication. FIG. 11 shows that various cutouts 28 can be utilized. For example, a large rectangular cutout 28 can separate two electrode portions. Alternatively, a multitude of differently shaped cutouts 28 can include circles, hexagons, triangles, squares, half-circles and the like. As can be appreciated by those skilled in the art, the present invention can be utilized in many of the ways the prior art electrodes have been utilized however now at a cheaper manufacturing cost.

It is understood herein that the cutouts 28 or voids 28 in any of the layers B, C or D can be used to control the conductivity/resistivity of any such layer. For example, to better control the current distribution in layer C, cutouts formed in layer C can be used. Alternatively, layer C may be screen printed or flood coated with various non-conductive inks 28 or with inks 28 having a higher resistivity than layer C. The cutouts 28 were a mechanical mechanism to control current distribution whereas the use of less conductive inks 28 is more of an electrical mechanism for controlling current distribution.

In efforts to achieve more control over the current distribution through layer C, it is possible to use two (or more) materials with differing resistivity. For example, layer C could comprise a graphite foil selectively cut and placed adjacently to an aluminum or tin foil. The graphite is more resistive in comparison to either aluminum or tin. Likewise, when the C layer is a gel layer with suspended conductive particles, two differing materials of conductive particles could be used. For example, particles of graphite may be used in one location whereas particles of aluminum or tin could be used elsewhere. In this manner the current distribution through the layer C can better be controlled while still resulting in a cheaper and simpler alternative to the prior art electrodes.

It is also to be understood that the electrodes 10 of the present invention can be made in varying shapes, including but not limited to, circles, squares, rectangles, triangles, ovals, ellipses, quatrefoils, curvilinear triangles, trapezoids, rhombuses, kites, pentagons, hexagons, heptagons, octagons, nonagons, decagons, parallelograms, crescents and any other shape possible as this disclosure is not limited to the shapes shown herein.

It is also be understood that in the present invention the layer C is a highly conductive layer whereas layers B and D are conductive. In other words, layer C is a layer which has a higher conductivity in comparison to layers B or D. It is also typical that gels and conductive foils are measured differently for resistivity, in that a foil is measured in a surface resistance whereas a gel is measured in a volume resistivity. In general the B layer and D layer will have a volume resistivity greater 100 ohm-cm and the C layer will have a surface resistivity less than 10 ohms. As can be seen, layer C is a highly conductive layer in comparison to layers B and D.

As one example of the present invention, the following measurements are applicable:

Layer B, USB35 gel, thickness 35 mils, volume resistivity 1233 ohm-cm, surface resistivity 6500;

Layer D, USS35 gel, thickness 34 mils, volume resistivity 1450 ohm-cm, surface resistivity 8600;

Layer C, graphite, thickness 5 mils, surface resistivity 4 ohm;

Layer C, aluminum, thickness 5 mils, surface resistivity 0.22 ohm;

Layer C, tin, thickness 2.5 mils, surface resistivity 0.08 ohm.

For further information, one is referred to U.S. Pat. No. 7,769,473 issued on Aug. 3, 2010, the contents of which are fully incorporated herein with this reference.

For further information, one is referred to U.S. Pat. No. 6,038,464 issued on Mar. 14, 2000, the contents of which are fully incorporated herein with this reference.

As used herein a mil is one thousandth of an inch, which is 0.001 of an inch.

Although several embodiments have been described in detail for purposes of illustration, various modifications may be made to each without departing from the scope and spirit of the invention. Accordingly, the invention is not to be limited, except as by the appended claims.

What is claimed is:

1. A dual-sided electrode pad assembly configured to be placed upon a patient's skin, the dual-sided electrode pad assembly comprising:
   an upper conductive gel layer having a volume resistivity greater than 100 ohm-cm;
   a middle conductive layer having a surface resistivity less than 10 ohms, and wherein the middle conductive layer comprises a conductive metallic foil or a gel layer with suspended conductive particles; and
   a lower conductive gel layer having a volume resistivity greater than 100 ohm-cm;
   wherein the middle conductive layer is disposed between the upper and lower conductive gel layers;
   wherein the upper conductive gel layer is configured to be in contact with an electrical connector or probe, the electrical connector or probe configured to transmit electrical energy first through the upper conductive gel layer, then second to the middle conductive layer, and then third to the lower conductive gel layer which is configured to be placed upon the patient's skin.

2. The dual-sided electrode pad assembly of claim 1, wherein the upper conductive gel layer is 5 to 50 mils thick.

3. The dual-sided electrode pad assembly of claim 1, wherein the upper conductive gel layer is approximately 20 mils thick.

4. The dual-sided electrode pad assembly of claim 1, wherein the upper conductive gel layer comprises hydrogel, silicone or hydrocolloid.

5. The dual-sided electrode pad assembly of claim 1, wherein the middle conductive layer is 0.1 to 10 mils thick.

6. The dual-sided electrode pad assembly of claim 1, wherein the middle conductive layer is approximately 1 mil thick.

7. The dual-sided electrode pad assembly of claim 1, wherein the suspended conductive particles in the gel layer of the middle conductive layer comprise metal particles, graphite particles or graphene particles.

8. The dual-sided electrode pad assembly of claim 1, wherein the lower conductive gel layer is 20 to 120 mils thick.

9. The dual-sided electrode pad assembly of claim 1, wherein the lower conductive gel layer is 40 mils thick.

10. The dual-sided electrode pad assembly of claim 1, wherein the lower conductive gel layer comprises hydrogel, silicone or hydrocolloid.

11. The dual-sided electrode pad assembly of claim 1, including a removable upper protective liner disposed on the upper conductive gel layer, wherein the upper protective liner is larger in surface area in comparison to the upper conductive gel layer, the middle conductive layer and the lower conductive gel layer.

12. The dual-sided electrode pad assembly of claim 1, including a removable lower protective liner disposed on the lower conductive gel layer, wherein the lower protective liner is larger in surface area in comparison to the upper conductive gel layer, the middle conductive layer and the lower conductive gel layer.

13. The dual-sided electrode pad assembly of claim 1, wherein the upper conductive gel layer is smaller in surface area in comparison to the middle conductive layer allowing a perimeter edge of the middle conductive layer to be disposed past an edge of the upper conductive gel layer.

14. The dual-sided electrode pad assembly of claim 13, wherein the lower conductive gel layer is larger in surface area in comparison to the middle conductive layer allowing a perimeter edge of the lower conductive gel layer to be disposed past the perimeter edge of the middle conductive layer.

15. The dual-sided electrode pad assembly of claim 1, wherein the upper conductive gel layer and the middle conductive layer generally have the same size of surface area, and wherein the lower conductive gel layer is larger in surface area in comparison to the upper conductive gel layer and the middle conductive layer allowing a perimeter edge of the lower conductive gel layer to be disposed past an edge of the upper conductive gel layer and the middle conductive layer.

16. The dual-sided electrode pad assembly of claim 1, wherein the middle conductive layer is smaller in surface area in comparison to the upper and lower conductive gel layers allowing a perimeter edge of the upper and lower conductive gel layers to be disposed past a perimeter edge of the middle conductive layer.

17. The dual-sided electrode pad assembly of claim 1, wherein the middle conductive layer comprises an indicia.

18. The dual-sided electrode pad assembly of claim 17, wherein the indicia is embossed into the middle conductive layer.

19. The dual-sided electrode pad assembly of claim 17, wherein the indicia is laser etched onto the middle conductive layer.

20. The dual-sided electrode pad assembly of claim 17, wherein the indicia is printed onto the middle conductive layer.

21. The dual-sided electrode pad assembly of claim 1, wherein the middle conductive layer comprises a plurality of individual middle conductive layers disposed between the upper and lower conductive gel layers.

22. The dual-sided electrode pad assembly of claim 1, including at least one cutout formed in the middle conductive layer.

23. The dual-sided electrode pad assembly of claim 1, including at least one cutout formed in either the upper or lower conductive gel layers.

24. The dual-sided electrode pad assembly of claim 1, including at least one cutout similarly formed in the upper conductive gel layer, the middle conductive layer and the lower conductive gel layer.

25. The dual-sided electrode pad assembly of claim 24, wherein the cutout comprises the shape of a circle, square, rectangle, triangle, oval, ellipse, quatrefoil, curvilinear triangle, trapezoid, rhombus, kite, pentagon, hexagon, heptagon, octagon, nonagon, decagon, parallelogram or crescent.

26. The dual-sided electrode pad assembly of claim 1, including at least one ink pattern disposed on the middle conductive layer, wherein the at least one ink pattern comprises a higher resistivity in comparison to the middle conductive layer.

27. The dual-sided electrode pad assembly of claim 1, wherein the conductive foil comprises at least two materials with differing resistivities.

28. The dual-sided electrode pad assembly of claim 1, wherein the suspended conductive particles of the gel layer comprise at least two materials with differing resistivities.

29. A dual-sided electrode pad assembly configured to be placed upon a patient's skin, the dual-sided electrode pad assembly comprising:
   an upper conductive gel layer, wherein the upper conductive gel layer is 5 to 50 mils thick and has a volume resistivity greater than 100 ohm-cm;
   a middle conductive layer comprising a conductive metallic foil, a conductive plastic film or a gel layer with suspended conductive particles, wherein the middle conductive layer is 0.1 to 10 mils thick and has a surface resistivity less than 10 ohms;
   a lower conductive gel layer, wherein the lower conductive gel layer is 20 to 120 mils thick and has a volume resistivity greater than 100 ohm-cm;
   wherein the upper and lower conductive gel layer comprise hydrogel, silicone or hydrocolloid;
   a removable upper protective liner disposed on the upper conductive gel layer, wherein the upper protective liner is larger in surface area in comparison to the upper conductive gel layer, the middle conductive layer and the lower conductive gel layer; and
   a removable lower protective liner disposed on the lower conductive gel layer, wherein the lower protective liner is larger in surface area in comparison to the upper conductive gel layer, the middle conductive layer and the lower conductive gel layer.

30. A dual-sided electrode pad assembly configured to be placed upon a patient's skin, the dual-sided electrode pad assembly comprising:
   an upper conductive gel layer, wherein the upper conductive gel layer is 5 to 50 mils thick and has a volume resistivity greater than 100 ohm-cm;
   a middle conductive layer comprising a conductive foil, a conductive plastic film or a gel layer with suspended conductive particles, wherein the middle conductive layer is 0.1 to 10 mils thick;
   a lower conductive gel layer, wherein the lower conductive gel layer is 20 to 120 mils thick and has a volume resistivity greater than 100 ohm-cm;
   wherein the upper and lower conductive gel layer comprise hydrogel, silicone or hydrocolloid;
   a removable upper protective liner disposed on the upper conductive gel layer, wherein the upper protective liner is larger in surface area in comparison to the upper conductive gel layer, the middle conductive layer and the lower conductive gel layer;
   a removable lower protective liner disposed on the lower conductive gel layer, wherein the lower protective liner is larger in surface area in comparison to the upper conductive gel layer, the middle conductive layer and the lower conductive gel layer; and
   wherein the middle conductive layer is smaller in surface area in comparison to the upper and lower conductive gel layers allowing a perimeter edge of the upper and lower conductive gel layers to be disposed past a perimeter edge of the middle conductive layer.

31. A dual-sided electrode pad assembly configured to be placed upon a patient's skin, the dual-sided electrode pad assembly comprising:
   an upper conductive gel layer;
   a middle conductive layer comprising a conductive metallic foil;
   a lower conductive gel layer;
   wherein the middle conductive layer is disposed between the upper and lower conductive gel layers;
   wherein the upper conductive gel layer is configured to be in contact with an electrical connector or probe, the electrical connector or probe configured to transmit electrical energy first through the upper conductive gel layer, then second to the middle conductive layer, and then third to the lower conductive gel layer which is configured to be placed upon the patient's skin.

32. A dual-sided electrode pad assembly configured to be placed upon a patient's skin, the dual-sided electrode pad assembly comprising:
   an upper conductive gel layer having a volume resistivity greater than 100 ohm-cm;
   a middle conductive layer having a surface resistivity less than 10 ohms; and
   a lower conductive gel layer having a volume resistivity greater than 100 ohm-cm;
   wherein the middle conductive layer is disposed between the upper and lower conductive gel layers;
   wherein the upper conductive gel layer is smaller in surface area in comparison to the middle conductive layer allowing a perimeter edge of the middle conductive layer to be disposed past an edge of the upper conductive gel layer;
   wherein the upper conductive gel layer is configured to be in contact with an electrical connector or probe, the electrical connector or probe configured to transmit electrical energy first through the upper conductive gel layer, then second to the middle conductive layer, and then third to the lower conductive gel layer which is configured to be placed upon the patient's skin.

33. A dual-sided electrode pad assembly configured to be placed upon a patient's skin, the dual-sided electrode pad assembly comprising:
- an upper conductive gel layer having a volume resistivity greater than 100 ohm-cm;
- a middle conductive layer having a surface resistivity less than 10 ohms; and
- a lower conductive gel layer having a volume resistivity greater than 100 ohm-cm;
- wherein the middle conductive layer is disposed between the upper and lower conductive gel layers;
- wherein the upper conductive gel layer and the middle conductive layer generally have the same size of surface area, and wherein the lower conductive gel layer is larger in surface area in comparison to the upper conductive gel layer and the middle conductive layer allowing a perimeter edge of the lower conductive gel layer to be disposed past an edge of the upper conductive gel layer and the middle conductive layer;
- wherein the upper conductive gel layer is configured to be in contact with an electrical connector or probe, the electrical connector or probe configured to transmit electrical energy first through the upper conductive gel layer, then second to the middle conductive layer, and then third to the lower conductive gel layer which is configured to be placed upon the patient's skin.

34. A dual-sided electrode pad assembly configured to be placed upon a patient's skin, the dual-sided electrode pad assembly comprising:
- an upper conductive gel layer having a volume resistivity greater than 100 ohm-cm;
- a middle conductive layer having a surface resistivity less than 10 ohms; and
- a lower conductive gel layer having a volume resistivity greater than 100 ohm-cm;
- wherein the middle conductive layer is disposed between the upper and lower conductive gel layers;
- wherein the middle conductive layer is smaller in surface area in comparison to the upper and lower conductive gel layers allowing a perimeter edge of the upper and lower conductive gel layers to be disposed past a perimeter edge of the middle conductive layer;
- wherein the upper conductive gel layer is configured to be in contact with an electrical connector or probe, the electrical connector or probe configured to transmit electrical energy first through the upper conductive gel layer, then second to the middle conductive layer, and then third to the lower conductive gel layer which is configured to be placed upon the patient's skin.

35. A dual-sided electrode pad assembly configured to be placed upon a patient's skin, the dual-sided electrode pad assembly comprising:
- an upper conductive gel layer;
- a middle conductive layer comprising a conductive metallic aluminum foil;
- a lower conductive gel layer;
- wherein the middle conductive layer is disposed between the upper and lower conductive gel layers;
- wherein the upper conductive gel layer is configured to be in contact with an electrical connector or probe, the electrical connector or probe configured to transmit electrical energy first through the upper conductive gel layer, then second to the middle conductive layer, and then third to the lower conductive gel layer which is configured to be placed upon the patient's skin.

36. A dual-sided electrode pad assembly configured to be placed upon a patient's skin, the dual-sided electrode pad assembly comprising:
- an upper conductive gel layer;
- a middle conductive layer comprising a gel layer with suspended conductive particles;
- a lower conductive gel layer;
- wherein the middle conductive layer is disposed between the upper and lower conductive gel layers;
- wherein the upper conductive gel layer is configured to be in contact with an electrical connector or probe, the electrical connector or probe configured to transmit electrical energy first through the upper conductive gel layer, then second to the middle conductive layer, and then third to the lower conductive gel layer which is configured to be placed upon the patient's skin.

* * * * *